US009980704B2

(12) United States Patent
Gratacós Solsona et al.

(10) Patent No.: US 9,980,704 B2
(45) Date of Patent: May 29, 2018

(54) NON-INVASIVE IMAGE ANALYSIS TECHNIQUES FOR DIAGNOSING DISEASES

(71) Applicant: TRANSMURAL BIOTECH, S. L., Barcelona (ES)

(72) Inventors: Eduard Gratacós Solsona, Barcelona (ES); Elisenda Bonet Carné, Barcelona (ES); Montse Palacio Riera, Barcelona (ES); Alvaro Pérez Moreno, Barcelona (ES); M$^a$ Teresa Cobo Cobo, Barcelona (ES)

(73) Assignee: TRANSMURAL BIOTECH, S.L., Barcelona (ES)

( * ) Notice: Subject to any disclaimer, the term of this patent is extended or adjusted under 35 U.S.C. 154(b) by 0 days. days.

(21) Appl. No.: 15/023,315

(22) PCT Filed: Sep. 20, 2013

(86) PCT No.: PCT/IB2013/058696
§ 371 (c)(1),
(2) Date: Mar. 18, 2016

(87) PCT Pub. No.: WO2015/040457
PCT Pub. Date: Mar. 26, 2015

(65) Prior Publication Data
US 2016/0242742 A1    Aug. 25, 2016

(51) Int. Cl.
*G06K 9/00* (2006.01)
*A61B 8/08* (2006.01)
*G06T 7/00* (2017.01)

(52) U.S. Cl.
CPC .......... *A61B 8/5223* (2013.01); *A61B 8/0808* (2013.01); *A61B 8/0866* (2013.01);
(Continued)

(58) Field of Classification Search
CPC ..... A61B 8/0808; A61B 8/085; A61B 8/0866; A61B 8/0883; A61B 8/0891;
(Continued)

(56) References Cited

U.S. PATENT DOCUMENTS

2003/0174872 A1* 9/2003 Chalana ................ G06K 9/00
                                                     382/128
2012/0078099 A1   3/2012 Suri

OTHER PUBLICATIONS

International Search Report and Written Opinion of PCT/IB2013/058696 dated Jul. 18, 2014; 16 pgs.
(Continued)

*Primary Examiner* — Siamak Harandi
(74) *Attorney, Agent, or Firm* — Maier & Maier, PLLC

(57) ABSTRACT

Techniques for assessing a tissue condition and diagnosing, assessing the prognosis of, or the risk for pathological conditions are disclosed. The technique may include an image acquiring module adapted to receive an image comprising at least a portion of animal or human tissue, a delineation module adapted to indicate an analysis zone in said acquired image, a feature extraction module adapted to extract quantitative information from said analysis zone and a machine learning module adapted to receive said extracted information and apply at least one detection algorithm to assess a condition of said tissue. The feature extractor module may have at least a rotation compensation module to compensate for the rotation of the analysis zone.

17 Claims, 3 Drawing Sheets

(52) U.S. Cl.
CPC .......... *G06K 9/0014* (2013.01); *G06T 7/0012* (2013.01); *A61B 8/085* (2013.01); *A61B 8/0883* (2013.01); *A61B 8/0891* (2013.01); *A61B 8/523* (2013.01); *G06K 2209/29* (2013.01); *G06T 2207/10132* (2013.01); *G06T 2207/20081* (2013.01); *G06T 2207/30044* (2013.01)

(58) Field of Classification Search
CPC .. A61B 8/5223; A61B 8/523; G06K 2209/29; G06K 9/0014; G06T 2207/10132; G06T 2207/20081; G06T 2207/30044; G06T 7/0012

See application file for complete search history.

(56) References Cited

OTHER PUBLICATIONS

Mohamend S S et al: "Prostate Cancer Spectral Multifeature Analysis Using TRUS Images", IEEE Transactions on medical imaging, IEEE service center, Piscataway, NJ, US, vol. 27, No. 4, Apr. 2, 2008, pp. 548-556, 9 pgs.

Magdalena Sanz-Cortes et al: "Automatic Quatitative MRI Texture Analysis in Small-for-Gestational-Age Fetuses Discriminates Abnormal Neonatal Neurobehavior", Plos One, vol. 8, No. 7, Jul. 26, 2013, 8pgs.

Montse Palacio et al: "Performance of an automatic quantitative ultrasound analysis of the fetal lung to predict fetal lung maturity", American Journal of Obstetrics and Gynecology, vol. 207, No. 6, Dec. 3, 2012, 6pgs.

\* cited by examiner

NON-INVASIVE IMAGE ANALYSIS TECHNIQUES FOR DIAGNOSING DISEASES

The present disclosure relates to diagnostic techniques and more specifically to non-invasive image analysis techniques for diagnosing diseases.

BACKGROUND ART

There are three main categories which describe the invasiveness of medical procedures. These are: non-invasive procedures, minimally invasive procedures, and invasive procedures. A medical procedure is strictly defined as non-invasive when no break in the skin is created and there is no contact with the mucosa, or skin break, or internal body cavity beyond a natural or artificial body orifice.

A category of non-invasive diagnostic techniques involves diagnosis via diagnostic imaging techniques. Such imaging techniques may include ultrasonography, dermatoscopy, magnetic resonance imaging (MRI) etc.

Non-invasive procedures have the benefit that they may cause no or minimal pain to the patient, no scarring, recovery is immediate, and the incidence of post-surgical complications, such as adhesions may be avoided. However, for a number of diseases, the diagnostic accuracy of non-invasive techniques may be questionable. In such cases, minimally invasive techniques may be used so medical technology has developed minimally-invasive methods, such as hypodermic injection (using the syringe), endoscopy, percutaneous surgery, laparoscopic surgery, coronary catheterization, angioplasty, stereotactic surgery, amniocentesis and many others.

Although minimally-invasive methods are considered safe and accurate for a number of diagnoses, a large number of patients may be reluctant to have them performed on their body for a number of reasons, discomfort being the most common one.

For the above reasons, it would be desirable to have a non-invasive imaging technique that may diagnose a disease with the same accuracy as a minimally invasive technique.

SUMMARY OF THE INVENTION

In a first aspect, a diagnostic device is proposed. The device may comprise an image acquiring module adapted to receive an image comprising at least a portion of animal or human tissue; a delineation module adapted to indicate an analysis zone in said acquired image; a feature extractor module adapted to extract quantitative information from said analysis zone; a machine learning module adapted to receive said extracted information and apply at least one detection algorithm to assess a condition of said tissue. The feature extractor module may comprise at least a rotation compensation module to compensate for the rotation of the analysis zone.

In some embodiments the image acquiring module is adapted to receive ultrasonic images. This may allow images of tissues of subcutaneous organs or entities to be processed by the device. As a result, a number of diseases that otherwise would require a minimally invasive procedure to be diagnosed may be analyzed by the device for assessing the condition of the tissue. In some embodiments the proposed device may further comprise an ultrasonic imaging module for acquiring the ultrasonic images.

In some embodiments the ultrasonic imaging module may have a fixed frequency range. This may allow reproducibility of results as the extracted features of two images that have been acquired with the same fixed frequency range may be directly comparable.

In some embodiments, for a specific condition to be assessed, the image acquiring module may be adapted to receive images corresponding to a particular anatomical plane. As a result all images pertaining to the same tissue may be directly comparable. This allows for the machine learning module to be trained effectively, thus increasing the accuracy of tissue assessment. To achieve this, the image acquiring module may be adapted to detect predefined landmarks in the received images.

In some embodiments the delineation module may comprise a drawing module adapted to allow a user of the device to mark the boundary of the analysis zone. The physician may manually mark that area of the image to be analyzed. The marking mode, also called delineation mode, may be defined first. The marking mode may either be a free-hand mode, where the physician may delineate the ROI, e.g. the fetal lung, by drawing a line by hand or by selecting the points between lines, or a polygon mode, where the physician may select a polygon type, e.g. a rectangle, and set the size of the polygon, or it may be an automatic mode. In the automatic mode the physician may select a point within the ROI and the software automatically delineates the ROI based on a pre-programmed delineation pattern. The selected point may be one of a plurality of landmarks that may be present in the image.

In some embodiments the feature extractor module may be arranged to extract quantitative information corresponding to first and second order statistical characteristics of the analysis zone. Statistical approaches have the advantage that they do not require any a priori modification or normalization since the information comes from the interactions between the pixels rather than from their values.

In some embodiments said statistical characteristics may be selected from a list including a mean value, a variance, a standard deviation, a skew and a kurtosis of the analysis zone or said characteristics may be obtained by gradients of the analysis zone either in the whole of or in portions thereof. Certain characteristics may be obtained by cascading. That is, after obtaining first order characteristics directly from the image or from the ROI, different characteristics may be obtained by applying different rotation parameters. For example by recursively rotating the image.

In some embodiments the feature extractor module may be further arranged to extract quantitative information corresponding to a characteristic orientation and a local phase of at least a portion of the analysis zone.

The characteristics obtained should be invariant to changes in lighting or shadows. With the techniques proposed hereof, the analysis may be invariant to geometric and photometric transformations. It should be noted that many of the methods described herein are also used for the detection of animals, people and objects such as cars, buses, dogs, pedestrians, etc. Other methods are used to detect facial expressions, audio applications, etc.

In some embodiments the feature extractor module is adapted to simultaneously extract quantitative information corresponding to a plurality of characteristics. The feature extractors should demonstrate invariant properties to one or more of the acquisition conditions. Therefore, for each particular problem several extractors may be used simultaneously, thus ensuring robustness under various acquisition conditions. For different extractors, the process may be considered to be robust when the robustness may be demonstrated within a certain range in the acquisition conditions that are not critical since in some cases certain the acquisition parameters may be controlled to some degree.

In some embodiments the machine learning module may be arranged to select from a plurality of algorithms depending on the characteristics used by the feature extractor module. As more than one feature extractor may be used, it is also possible to use more than one learning algorithm.

In some embodiments the machine learning module may be arranged to combine a plurality of algorithms to assess said condition of said tissue. The final result obtained by introducing a new sample may come from the result of a vote of the different learning algorithms used. In that case, the number of algorithms that participate in the vote may be odd.

In some embodiments the machine learning module may comprise a memory for storing quantitative information corresponding to characteristics of a plurality of images corresponding to said condition. Therefore, the device may compare the characteristics of the acquired image with the characteristics of the stored images to assess the condition of the tissue.

In some embodiments the condition may be a neonatal respiratory morbidity condition and said tissue may be fetal lung tissue. Therefore, with the use of the proposed device any minimally invasive technique, such as amniocentesis, may be avoided.

In other embodiments the condition may be a neurological or neurodegenerative condition, such as Alzheimer's disease and said tissue may be a frontal or temporal brain lobe tissue.

In other embodiments the condition may be a cardiovascular condition and said tissue may be the heart or any cardiovascular tissue.

In other embodiments the condition may be a brain damage and said tissue may be brain tissue.

In other embodiments the condition may be an organ tumor condition and said tissue may be organ tissue.

In other embodiments the condition may be a condition related with the wellbeing of transplanted tissue and said tissue may be any transplanted organ tissue.

In other embodiments the condition may be a tissue degeneration, also referred to as tissue inflammation, at a parenchyma in the body. Such parenchyma may be at a kidney, liver or other organ of the body.

In another aspect, a method of assessing a risk associated with a condition of at least a portion of an animal or human tissue is disclosed. The method may comprise receiving an image of said at least one portion of animal or human tissue; indicating an analysis zone in said received image; extracting quantitative information from said analysis zone; and, applying a machine learning algorithm to said extracted quantitative information to assess the condition of said tissue. Said extracting quantitative information may comprise at least compensating for a rotation of the analysis zone.

In yet another aspect; a method of diagnosing a pathological condition of at least a portion of an animal or human tissue is disclosed. The method may comprise receiving an image of said at least one portion of animal or human tissue; indicating an analysis zone in said received image; extracting quantitative information from said analysis zone; applying a machine learning algorithm to said extracted quantitative information to assess the condition of said tissue. Said step of extracting quantitative information may comprise at least compensating for a rotation of the analysis zone. If the extracted quantitative information corresponds to stored quantitative information belonging to animal or human tissue of said pathological condition, then said portion of animal or human tissue may be diagnosed of said pathological condition.

In yet another aspect, a diagnostic device is disclosed. The device may comprise electronic means for receiving an image of said at least one portion of animal or human tissue, electronic means for indicating an analysis zone in said received image, electronic means for extracting quantitative information from said analysis zone and electronic means for applying a machine learning algorithm to said extracted quantitative information to assess the condition of said tissue.

In yet another aspect, a computing device is disclosed. The device may comprise a memory and a processor. The memory may store computer program instructions executable by the processor, said instructions comprising functionality to execute a method of assessing a condition of at least a portion of an animal or human tissue according to the above mentioned aspects hereof.

In yet another aspect, a computer program product is disclosed. The program may comprise instructions to provoke that a diagnostic device implements a method of assessing a condition of at least a portion of an animal or human tissue according to the above mentioned aspects hereof.

In some embodiments the computer program product may be stored in recording media and in other embodiments it may be carried by a carrier signal.

Additional objects, advantages and features of embodiments of the invention will become apparent to those skilled in the art upon examination of the description, or may be learned by practice of the invention.

BRIEF DESCRIPTION OF THE DRAWINGS

Particular embodiments of the present invention will be described in the following by way of non-limiting examples, with reference to the appended drawings, in which.

DETAILED DESCRIPTION OF EMBODIMENTS

Figure 1:
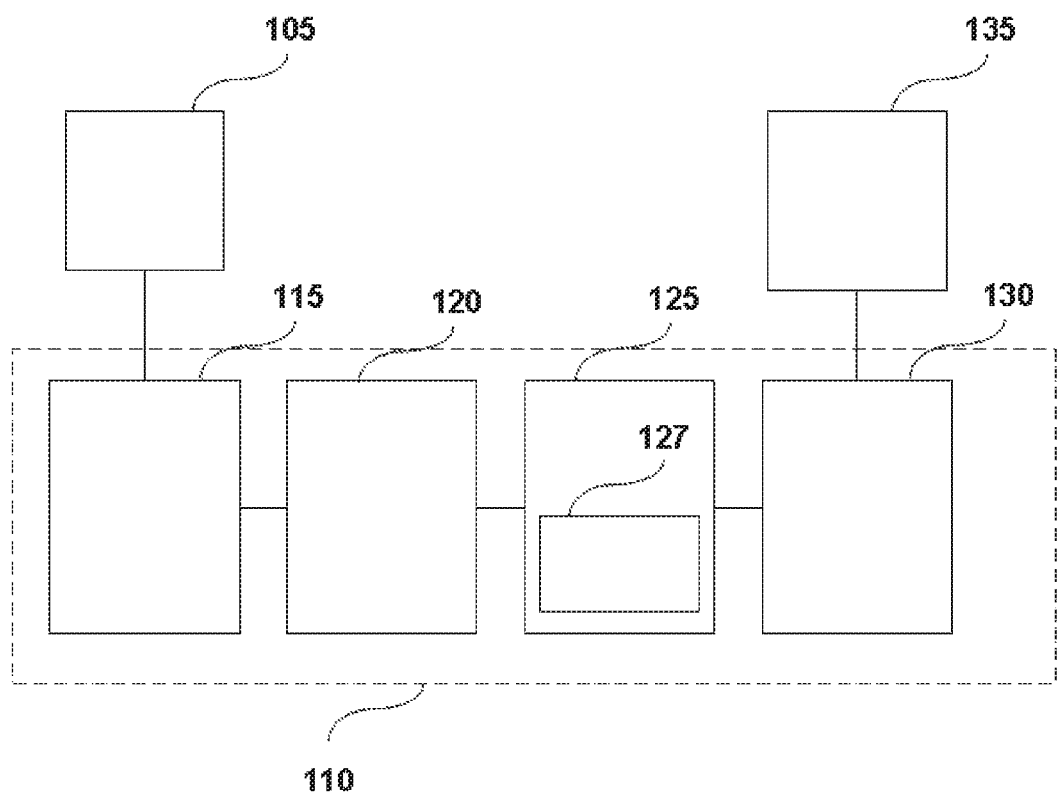
FIG. 1 is a block diagram of a device for assessing a tissue condition according to an embodiment.

FIG. 1 is a block diagram of a device for assessing a tissue condition according to an embodiment. Device 110 comprises image acquiring module 115, delineation module 120, feature extraction module 125 and machine learning module 130. The image acquiring module 115 may be connected to an imaging equipment 105. The imaging equipment 105 may record and/or store tissue images that may be subsequently processed by the device 110. In some embodiments the imaging equipment 105 may form part of the image acquiring module 115 or of the device 110 or be externally connected to device 110. Such external connection may be wired or wireless. The imaging equipment 105 may be any type of imaging apparatus suitable to record and/or store an image that may be used to visually represent a tissue portion of an organ of a human or an animal. In one example the imaging equipment is an ultrasonic imaging module adapted to record ultrasonic images. The feature extraction module 125 further includes a rotation compensation module 127. Its function is explained further below.

To achieve a certain level of reproducibility and in order for the acquired images to be comparable, the imaging equipment 105 and/or the image acquiring module 115 may be parameterized according to the requirements of the specific application. For example, in the case of a condition known as neonatal respiratory morbidity, the following parameters should be set for the acquisition of the images:

The frequency range of the imaging equipment 105, which in this case would be an ultrasonic imaging module, should be between 2 MHz and 6 MHz. Any type of post-processing, such as smoothing, should be disabled so that the characteristics of the image are not affected by any software of the imaging module. The acquired image should be a two-dimensional (2D) ultrasound image corresponding to a particular anatomical plane.

Figure 3A:
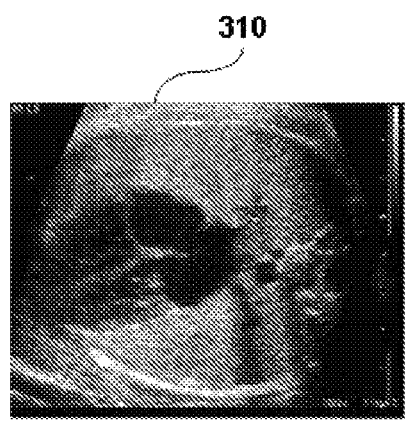
FIG. 3A shows an image of a part of a fetus as acquired by an ultrasonic device.
Figure 3B:
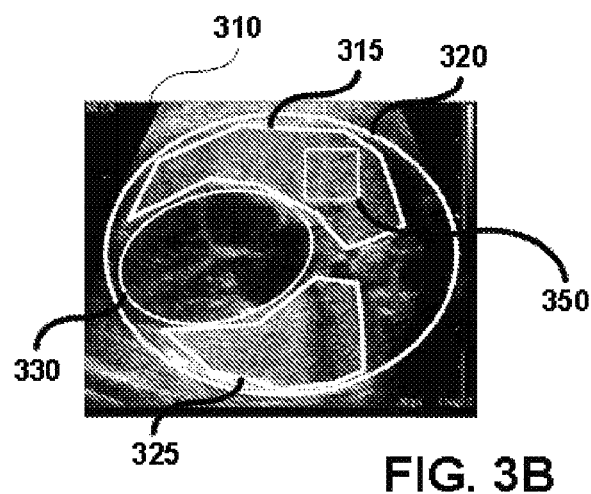
FIG. 3B shows the image of FIG. 3A delineated to indicate visible organs of the fetus and an analysis zone.
Figure 3C:
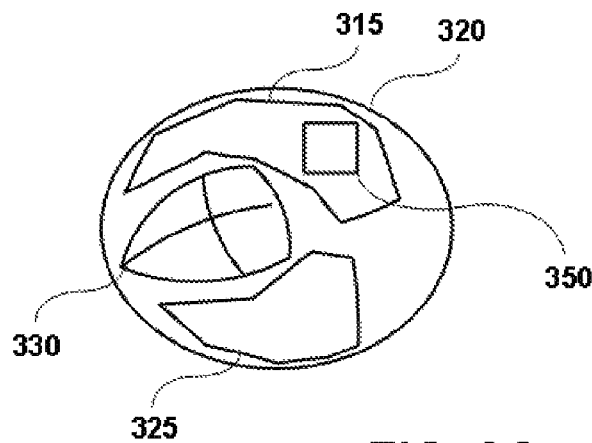
FIG. 3C shows a landmark guide to be used as reference during the acquisition and delineation of an image.

FIG. 3A shows an image of a part of a fetus as acquired by an ultrasonic device. The image of FIG. 3A is an example of an image of a portion of a fetus that is suitable for reception and processing by the device 110. Furthermore, a plurality of well-established landmarks is present in the image. For example, as indicated in FIG. 3B, the plane is a semi-lateral section depicting distinguishable organs such as the heart 330 and its four (4) heart chambers, the lungs 315, 325, and the thorax 320. A landmark guide, as the one depicted in FIG. 3C may be used during the acquisition and delineation phase to assure that the acquisition plane is repeatable and comparable. There should be no shadows or saturation in the images. No zoom function, insofar as possible, may be used during the acquisition of the image, as this may affect the characteristics thereof. However, depth adjustment may be employed if it is available as it enhances the characteristics and facilitates any subsequent extraction. The image acquired should be free of any artifacts, voluntary or involuntary, such as calipers, pointers, measurements, etc.

One skilled in the art may appreciate that the anatomy, physiology and physical conditions of the subject (e.g. the fetus) are factors that should be taken into account during acquisition since no two subjects are identical. Furthermore, the scanning technique depends on the knowledge and experience of the sonographer.

In the case of ultrasound imaging, the acquired image may be stored in DICOM format as well as contain any image metadata that may be useful for the proper analysis of the image. For example, the resolution of the image should be stored.

Apart from the acquired image, further characteristics of the subject, i.e. clinical data should be acquired. These may include accurate information corresponding to the time of the image acquisition. Such information may be the age of the subject (e.g. gestational age of the fetus), the weight etc. This information may be used by the predictive algorithms during the condition assessment phase of the process.

Once the image has been properly acquired, the area in the image that is to be analyzed should be determined. The delineation module 120 may be used to indicate the analysis zone or region of interest (ROI). A ROI 350 is depicted in FIG. 3B. The physician may manually mark that area of the image to be analyzed. The marking mode (or delineation) may be defined first. The marking mode may either be free-hand mode, where the physician delineates the ROI, e.g. the fetal lung, by drawing a line by hand or by selecting the points between lines, or polygon mode, where the physician may select a polygon type, e.g. a rectangle, and set the size of the polygon, or it may be automatic mode. In the automatic mode the physician may select a point within the ROI and the software automatically delineates the ROI. The selected point may belong to one of the plurality of landmarks that may be present in the image. In FIG. 3B a rectangle ROI 350 is shown. However, the entire lung zone 315 may be used or any other ROI within the lung zone 315 that may fulfil a set of criteria. For the proper functioning of the algorithm, the ROI should have a minimum size and it should not contain artefacts, such as shadows or portions of saturated image and it may not contain structures or tissue or regions apart from the ROI.

To better understand the requirements of the ROI, the example case of neonatal respiratory morbidity will be explained in detail:

The most common respiratory problem in preterm infants is the respiratory distress syndrome. Other respiratory problems may appear in pregnancies before gestational week 39, mainly transient tachypnea. All these problems may altogether be defined as neonatal respiratory morbidity, i.e. the presence of respiratory problems in a newborn that may require admission of the newborn to a special unit and the use of medical respiratory support. Respiratory morbidity is very common in preterm newborns, particularly before 34 weeks, and it is less common as the gestation progresses towards full term (40 weeks) but it can occur at any gestational age, particularly before 39 weeks of gestation. The term "fetal lung maturity" is universally used by the scientific and medical community to define the capacity of fetal lungs to achieve normal respiratory function if the fetus is born.

The lung architecture itself and mainly the concentration of surfactant may determine fetal lung maturity, and consequently the risk of respiratory morbidity. In the last stages of lung development, the histological architecture of the lung changes rapidly and progresses towards the development of terminal sacs which will become alveoli, the structures that allow respiration in postnatal life. From approximately gestational week 24, pneumocytes type H, the cells producing surfactant, will appear and increase in number progressively until full term. The surfactant is composed primarily of phospholipids (80-90%) and proteins (10%) with a small amount of neutral lipids, and it is a critical substance to allow the alveoli to be expanded during respiration, and consequently to ensure normal respiration. Respiratory morbidity in newborns is caused in most instances by an insufficient amount of surfactant and, as mentioned it can also be influenced by the developmental stage of the lung. These factors may vary substantially in each individual fetus for the same gestational week.

The proposed device may detect differences in the composition of the lung tissue to determine the risk of a fetus of having neonatal respiratory morbidity, as defined above.

Each tissue may have a different acoustic response to ultrasound waves. However, in order to detect the acoustic response of a region of interest it is important to define the region from which there is an interest to extract information.

The region of interest may be the fetal lung parenchyma. The structures that should be avoided to be included in the ROI making the delineation are primarily the heart and secondarily any part other than lung. Also any lung area that may contain large blood vessels should also be avoided when delineating.

The size of the ROI in the case of fetal lung should be at least 400 pixels, in order to contain sufficient information in order to extract enough features to characterise the tissue. For optimal performance, the system should include a ROI of more than 1600 pixels.

Apart from any blood vessels that should not be delineated, the ROI, as already mentioned, should also avoid to include any other image artifacts. Therefore, the ROI should neither contain shadows nor be saturated or dark because the pixels must contain sufficient information so that it can be extracted by the feature extractor module 125.

Furthermore it should not include bookmarks, guides or any artificial lines as nothing should be included in the delineated structure other than the structure of interest, e.g. the fetal lung.

The acquisition module 115 may specify the type of images that may be valid for the analysis. Therefore, this may serve as an indication for the delineation requirements.

The feature extraction module 125 allows the extraction of quantitative information in the ROI of an image. This information may consist of a series of numerical values that constitute the features of the image.

In image processing, the concept of a "feature" is used to refer to a "piece" (or numerical value) of information that is relevant to the solution of the calculation to be performed for a given application.

In the example case of neonatal respiratory morbidity, the features may be extracted from the ROI of the image of the fetal lung. Although the acquisition plane and the acquisition parameters may be defined in each section, it is still necessary that the feature extraction algorithms used are robust to acquisition variations produced due to clinical reasons.

The extraction algorithm being robust to a particular acquisition parameter implies that the extracted features of the image must be the same (or nearly the same) when the parameter changes.

If the extraction algorithm is robust to the acquisition parameters, then the extracted parameters may be directly linked to information obtained from the image. It is generally accepted that ultrasound images permit the detection of changes in the structures at a cellular level.

Therefore, any disease, syndrome or clinical change that involves a subtle or not subtle change in the tissue that is to be analyzed, should be detectable by extracting the correct features from the ROI of the image.

Each application may have different levels of acquisition, ROI and different acquisition parameters that may influence the choice of one or other feature extraction algorithms and these may be based on different image processing methods for the extraction of the information.

Although each application may involve different parameters that the feature extractor module must be robust to, in the case of neonatal respiratory morbidity these parameters may include, for example:

Lighting. The ultrasound images may be more or less bright based on the gain of the ultrasonic equipment. They may also have different tones and different chromatic scales according to the configuration of the ultrasonic equipment 105 or the image acquisition module 115. If the ultrasound image (or the corresponding ROI) is not saturated (i.e. if the ROI is white without "texture") or dark (i.e. if the ROI is black without "texture"), that means that no information is added by the colour in which it is represented and the overall brightness of the image should not influence the outcome of the extracted features.

Resolution. The resolution of the image may not be a configurable parameter in all imaging equipment. Although in most clinical applications (what one wants to see) the operating frequency range of the transducer is fixed, in many cases this frequency range it is not known. Being unable to control the acquisition frequency, the resolution of the image may also be different in each case. However, the type of information that may be extracted from the ROI should always be the same even if the resolution is different.

Rotation. With respect to the example of fetal chest images, these may not always be acquired from the same perspective as the fetus may move within the womb of the mother. It is therefore important that the extraction algorithms are invariant to rotation. For example, they may operate in the same way that the text "extractors" recognize text either if the text is horizontal or not. Accordingly, as mentioned above, the feature extractor module 125 of the device 110 further comprises a rotation compensation module 127 to account for the different rotations of the images so that the features extracted may be the same regardless of the image or ROI rotation.

Angle of insonation/acquisition plane. Although it is possible to define clear guidelines to pre-define the ideal acquisition plane (landmarks), there is no assurance that the actual acquisition will be exactly in the same plane. The feature extractor should extract the same features even if the plane is different. In the example of neonatal respiratory morbidity, the feature extraction should be invariant to 3D rotation of the fetus. Although the insonation angle may be different, the ROI must belong to fetal lung.

Size/shape of the ROI. Although it doesn't belong directly to the acquisition process, it belongs to one of the input variables of the feature extraction module. The feature extraction algorithms must be robust to the size and shape of the ROI as this may be different in each case (e.g. if the delineation is in manual mode) but the result should always be the same. In general, the extractor must obtain information related, in this example, to lung tissue of the region of interest and not from any other parameter. Thus, although there are differences in the parameters of acquisition, if the tissue to be analyzed is the same, the extracted information will also be the same.

Many methods for extracting characteristics may be used as part of the invention. One example are texture based methods. These methods quantify the texture of the image, i.e., the spatial arrangement of the color intensities. To extract information based on textures this may be implemented based on structural or statistical approaches.

Statistical approaches have the advantage that they do not require any a priori modification or normalization since the information comes from the interactions between the pixels rather than from their values.

Some of the feature extraction algorithms that may be suitable may be based on:

First order statistics features that may be obtained from a matrix of co-occurrence. These features may be obtained by looking at the spatial relationships of similarly grey levels in a region of an image. Other features such as the angular second moment, contrast, correlation, energy and entropy may also be calculated from the co-occurrence matrix.

Statistical characteristics of first and second order of the image or of the ROI. From the ROI one may obtain the mean, variance, standard deviation, the skew and kurtosis of the image.

Features obtained from the occurrence of different orientations of gradients both in the whole of and in local portions of the ROI obtained from a coarse and fine spatial sampling.

Features obtained by cascading. That is, after obtaining first order characteristics directly from the image or from the ROI, different characteristics may be obtained by applying different rotation parameters. For example, these characteristics may be obtained by recursively rotating the image.

Certain characteristics may be obtained in different layers of the image.

Features that model the phase and angular distribution.

The gradients of an image. For each pixel of the image a gradient may be obtained. Then the image may be divided in cells achieving a predetermined number of gradients in each cell. In each cell, the gradients that meet a certain restriction of the angle may be summed. Every feature should correspond to the value obtained by the sum of the gradients, so that the number of features may correspond to the number of cells in each image.

The characteristics obtained should be invariant to changes in lighting or shadows. Furthermore, the above mentioned methods should be invariant to geometric and photometric transformations. Thus, many of the methods described are also used for the detection of objects, animals and people as cars, buses, dogs, pedestrians, etc. Other methods are used to detect facial expressions, audio applications, etc.

One skilled in the art may appreciate that in an actual clinical environment and according to the medical application, there will be different ROI acquisition or operation conditions that may not be controlled. For example, in fetal ultrasound examinations, due to the movement of the fetus, the distance between the transducer and the organ of interest may not be fixed, or the angle of insonation, etc. The aim should be that when extracting information from two images at different acquisition conditions of the target object under study (for example, an organ of the same patient), the same set of features is obtained. It should be noted that the robustness against acquisition conditions ensures that the features do not contribute information about the condition itself and, therefore, that they are directly related to the clinical problem that is to be treated depending on each medical application.

The proposed feature extraction methods demonstrate invariant properties to one or more of the acquisition conditions. Therefore, for each particular problem several extractors may be used simultaneously, thus ensuring robustness under various acquisition conditions. For different extraction algorithms, the process may be considered to be robust when the robustness may be demonstrated within a certain range in the acquisition conditions that are not critical since in some cases only some acquisition parameters may be controlled to some degree.

Finally, the obtained descriptors or characteristics may serve as input for the learning system. Given that a posteriori a predictive model is applied, when the feature extractor methods are selected, certain aspects should be taken under consideration. For example, the number of features must be set for each application. So that always the same number of features may be obtained. For example, in the fetal lung case, the combination of extractors may provide two feature vectors of 81 and 256 characteristics, respectively. The 81 characteristics may be ordered according to a technique that counts occurrences of gradient orientation in localized portions of an image. Firstly, this method may compute a gradient for each pixel of the image. Then, in a second step, the cell histograms may be created. In order to create the cell histograms, the image may be divided in cells achieving a predetermined number of gradients in each cell. In the example case of the image of a fetal lung, the ROI may be divided in 3×3 cells of the same size. In each cell, the gradients that meet a certain restriction of different angle may be summed to assemble the histogram. In this manner, the number of angles may correspond to the number of bins of the histogram. In order to compensate the changes in illumination and contrast, the gradient may be normalized. Finally, every feature may correspond to the value obtained by the sum of the gradients in each cell, so that the number of features corresponds to the number of cells in each image and the number of bins. In the example case, there are 9 (nine) bins, thus obtaining 81 features.

The 256 characteristics may be derived from a texture based method that compensates for the rotation of the image. This method may extract features by means of two stages. In a first stage, a local characteristic orientation may be estimated. In a second stage, a descriptor vector may be extracted. In the first stage, the local characteristic orientation may be computed using a complex moment based on the Fourier Transform. Once the characteristic orientation is extracted, a procedure based on the examination of the local phase in local neighbourhoods at each pixel position may be applied. To examine the local phase, a discrete short term Fourier transform may be used applying a window function that defines the neighbourhood and the computation of the local Fourier coefficients at four frequency points. By means of the signs of the real and imaginary parts of each local Fourier coefficients, eight binary coefficient may be obtained. These resulting coefficients may be represented as integer values between 0-255. A histogram of these values from all positions may be assembled to obtain 256 characteristics. In order to compensate the rotation of the image that has to be analyzed, the direction of the characteristic may be considered in the examination of the local phase. In this manner, the final features extracted may be the same regardless of the image or ROI rotation.

These 337 characteristics (81+256) may be grouped together with clinical characteristics. In the example of the assessment of fetal lung maturity an extra characteristic may be the gestational age of the fetus. Therefore a total of 338 characteristics may be introduced to the machine learning module 130 to assess the fetal lung maturity.

Once the characteristics of the ROI of the ultrasound image have been extracted, it is necessary to apply a model (or an algorithm) that may combine the characteristics to obtain the desired result. For example, in the case of the assessment of fetal lung maturity the presence of a high or low risk of neonatal respiratory morbidity shall be assessed.

The manner in which the features may be combined is defined by the learning algorithm used to generate the model.

The proposed system is analogous to a standard diagnostic system:

The extraction of features of the image would be analogous to the removal of a biological sample (e.g. taking a blood sample).

The learning algorithm would be analogous to that obtained from a hemogram. That is, it may separate the characteristics of interest from the other characteristics and combine them to produce meaningful information.

The result may be the interpretation of the data obtained by the learning algorithm(s).

In general, an analogy could be made of a prediction system to an acoustic biopsy or histology by means of an image.

Several machine learning or computer vision algorithms may be used. In a similar manner as more than one feature extractor may be used, it is also possible to use more than one learning algorithm. In the example of the neonatal respiratory morbidity condition, according to the gestational age, a first separation of algorithms may take place. This may be done by using different algorithms for lungs that may be in various stages of development: For example, different algorithms for the canalicular, the saccular or the alveolar phase.

Similarly, for each gestational age range multiple algorithms (models) may be used. The applied learning models (algorithms) may be generated using a plurality of samples. In one example, 328 images were sampled according to acquisition restriction discussed above. The images may be stored in a database such as database 135. The database 135 may be part of the machine learning module 130 or it may be remotely connected to machine learning module 135. This has the benefit that many distributed machine learning modules may use the same database. Thus, the characteristics that the system would recognize shall be, mainly, due to changes in the tissue and not to any other acquisition parameter.

The several learning algorithms that may be used are similar to those used for face detection, palm reading, license plate recognition etc.

The different algorithms share the same principle: to identify and match automatically those features useful for predicting e.g. the risk of neonatal respiratory morbidity (or any other condition of interest).

Once the model is generated, for each new sample that enters the system the machine learning module 130 only needs to apply the final model (coded in software) and this will return the desired prediction result.

The software, representing the final model or algorithm, should be capable of operating under various conditions. That means, for example, operating with different resolutions, lighting, ultrasound equipment, etc. It is therefore important to train the system with images that present a diversity of features.

The feature extraction algorithms used may play an important role in this regard because they provide the same (or similar) characteristics when there are variations in the same parameters.

Various models may be used to generate the final model (final algorithm). The final result obtained by introducing a new sample may come from the result of a vote of different learning algorithms used. The number of algorithms that participate in the vote may be odd.

In the example of neonatal respiratory morbidity, according to the gestational age group, the algorithms that make the final system may vary. Similarly, the combination of these groups of learning algorithms may provide one and only algorithm for each group, and therefore, for each new sample to be analyzed.

To generate the different algorithms, supervised learning techniques may be used, where the value of the output is known (e.g. the outcome, if the image corresponds to a fetus that breathed or not) and may have some input variables, such as those obtained by the feature extractors combined with clinical data. The objective of these algorithms is to find a function that, starting from the input values, may estimate an output with the lowest cost (the minimum possible mistakes).

To generate the different models the concept of "boosting" may be used, by using different computational bases in either generic mode, or adaptive mode or in "gradient boosting" mode. The "boosting" may generate different models and weights to iteratively obtain a single prediction. In some algorithms "gradient boosting" may be used that involves some changes in the function of cost.

As a base algorithm of the learning algorithms regression trees and networks may be used. For the different bases of the algorithms generated by means of "boosting", classifier sequences may be generated, which in turn may be combined to achieve the best prediction.

For the base algorithms that may not define a cost function, only a part of the sample may be used (a technique known as "random undersampling") that may be recalculated at each iteration to apply the principle of "boosting".

The base algorithms used for different algorithms may be regression trees. In generating an algorithm a plurality of samples may be used (algorithms that were not used by the various boosting methods) to identify and select which combinations of algorithms may produce the best prediction. Furthermore, for each selection it should be confirmed that the features used by the algorithms come from different extraction methods to provide the necessary information in different acquisition circumstances.

The different algorithms chosen for different clinical data, e.g. each gestational age in the example of neonatal respiratory morbidity, may be those used in the final voting system to obtain the final result. In conclusion, through the different combinations of extractors and algorithms a product sturdy to various parameters of interest may be provided.

The result of the applied final algorithm may be the likelihood of an outcome or not. For example, a result may be given with:

High or low probability of having the disease without specifying the degree of probability, Specifying the degree of probability of having the disease given the percentage corresponding to the probability of having the disease.

Figure 2:
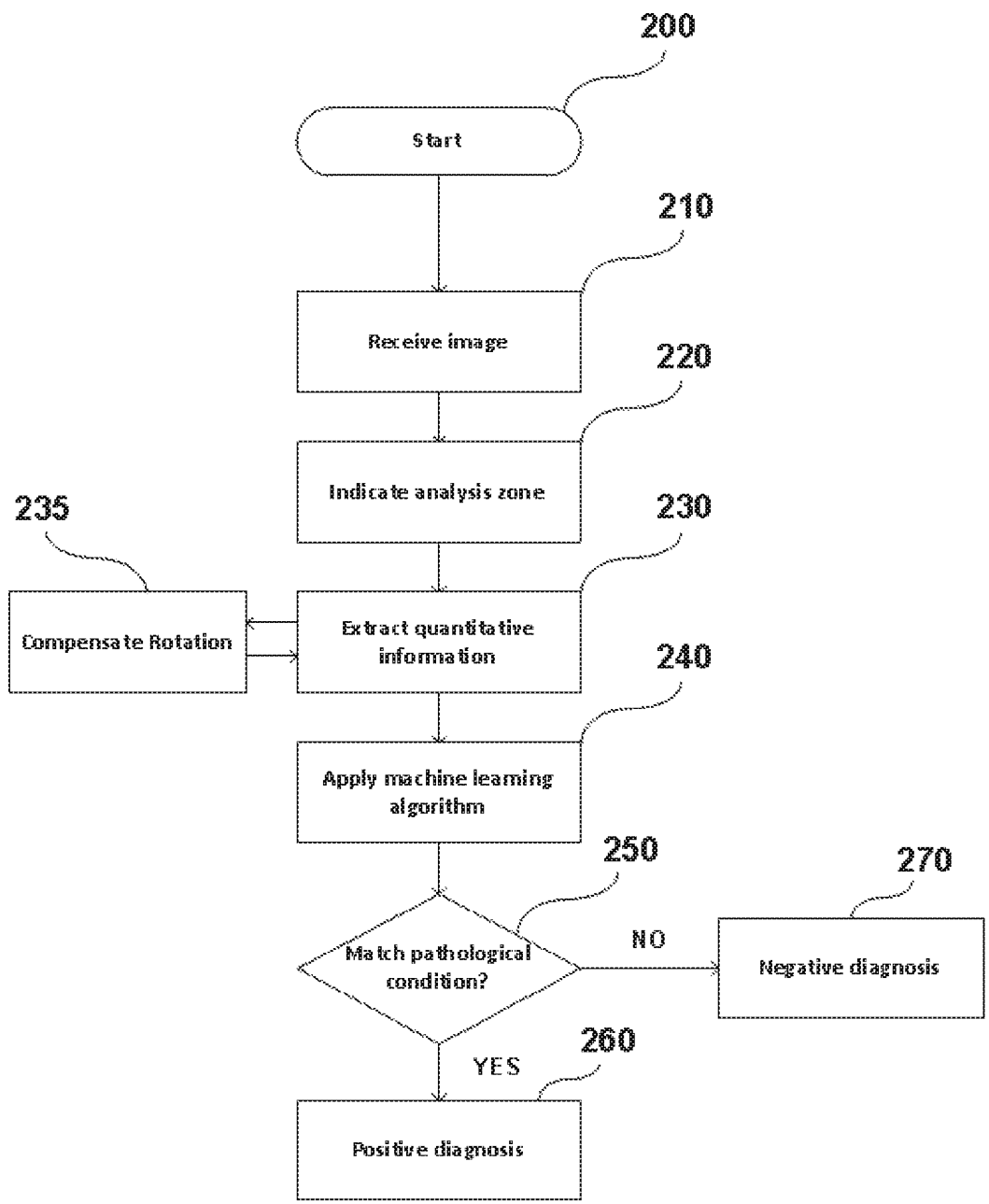
FIG. 2 is a flow diagram of a process of assessing a condition of a portion of a tissue according to another embodiment.

FIG. 2 is a flow diagram of a process of diagnosing a pathological condition of a portion of a tissue according to another embodiment. In a first step 200 the diagnostic process is initiated. In step 210, an image is received. The image should have some minimum attributes as discussed above so that the analysis may be repeatable and robust. In step 220, an analysis zone is indicated. Accordingly, the analysis zone should have some minimum characteristics as discussed above with reference to FIG. 1. In step 230, quantitative information is extracted from the ROI indicated in the previous step. During the extraction of information the rotation of the ROI is compensated in step 235. Such compensation should be performed with respect to all similar images used for training the machine learning module. After the quantitative information has been extracted, the extracted characteristics are used as input to the machine learning algorithm. The algorithm, already trained by a plurality of similar images is adapted to perform a comparison of the characteristics and predict a pathological condition based on a possible match between the extracted characteristics and the characteristics already used for the machine training process. This matching takes place in step 250. If there is a match, then in step 260 the diagnosis is positive. Otherwise, in step 270, the diagnosis is negative or non-conclusive.

Although the device and method have been described with the example of neonatal respiratory morbidity condition assessment and corresponding diagnosis of a pathological condition of said fetal lung, one skilled in the art may appreciate that the proposed technique may be used for other types of images and other tissue conditions. Examples of such conditions may be a neurological or neurodegenerative condition, such as an Alzheimer condition, where said tissue may be a frontal or temporal brain lobe tissue, a cardiovascular condition and said tissue may be a heart or any cardiovascular tissue, a brain damage and said tissue may be brain tissue or an organ tumour condition and said tissue may be the respective organ tissue, a condition related to the wellbeing of transplanted tissue and said tissue may be a transplanted organ tissue or a tissue degeneration at a parenchyma of the body. In the latter case said parenchyma may belong to any relevant organ such a kidney, a liver or the like.

Although only a number of particular embodiments and examples of the invention have been disclosed herein, it will be understood by those skilled in the art that other alternative embodiments and/or uses of the invention and obvious modifications and equivalents thereof are possible. Furthermore, the present invention covers all possible combinations of the particular embodiments described. Thus, the scope of the present invention should not be limited by particular embodiments, but should be determined only by a fair reading of the claims that follow.

Further, although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source code, object code, a code intermediate source and object code such as in partially compiled form, or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means.

When the program is embodied in a signal that may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

The invention claimed is:

1. A device comprising:
   an image acquiring module adapted to receive an image comprising at least a portion of animal or human tissue;
   a delineation module adapted to indicate an analysis zone in said acquired image;
   a feature extractor module adapted to extract quantitative information from said analysis zone;
   a machine learning module adapted to receive said extracted information and apply at least one detection algorithm to assess a condition of said tissue,
   wherein the feature extractor module comprises at least a rotation compensation module to compensate for the rotation of the analysis zone,
   wherein the feature extractor module is further arranged to extract quantitative information corresponding to at least one of the following:
      characteristics calculated from a co-occurrence matrix of said analysis zone;
      first and second order statistical characteristics of the analysis zone;
      characteristics obtained by gradients of the analysis zone in one of a whole of or in portions thereof;
      characteristics obtained by cascading;
      a characteristic orientation and a local phase of at least a portion of the analysis zone
   wherein the feature extractor module is adapted to simultaneously extract quantitative information corresponding to a plurality of characteristics,
   wherein the machine learning module is arranged to select from a plurality of algorithms depending on the characteristics used by the feature extractor module, and
   wherein the machine learning module is further arranged to combine a plurality of algorithms to assess said condition of said tissue.

2. The device according to claim 1, wherein, for a specific condition to be assessed, the image acquiring module is adapted to receive images corresponding to a particular anatomical plane.

3. The device according to claim 2, wherein the image acquiring module is adapted to detect predefined landmarks in the received images to determine if the received image corresponds to the particular anatomical plane.

4. The device according to claim 1, wherein the delineation module comprises a drawing module adapted to allow a user of the device to mark the boundary of the analysis zone.

5. The device according to claim 4, wherein said drawing module comprises a free-hand module to allow the user to manually indicate said boundary.

6. The device according to claim 4, wherein said drawing module comprises a polygon module to allow the user to indicate said boundary.

7. The device according to claim 1, wherein said characteristics calculated from a co-occurrence matrix of said analysis zone are selected from a list including first order statistics, an angular second moment, a contrast, a correlation, an energy and an entropy of said analysis zone.

8. The device according to claim 1, wherein said first and second statistical characteristics of the analysis zone are selected from a list including a mean value, a variance, a standard deviation, a skew and a kurtosis of the analysis zone.

9. The device according to claim 1, wherein the machine learning module comprises a memory for storing quantitative information corresponding to characteristics of a plurality of images corresponding to said condition.

10. A method of assessing a condition of at least a portion of an animal or human tissue, comprising:
   receiving an image of said at least one portion of animal or human tissue;
   indicating an analysis zone in said received image;
   extracting quantitative information from said analysis zone;
   applying a machine learning algorithm to said extracted quantitative information to assess the condition of said tissue;
   wherein said extracting quantitative information comprises at least compensating for a rotation of the analysis zone, wherein said extracting quantitative information comprises extracting quantitative information corresponding to at least one of the following:
- characteristics calculated from a co-occurrence matrix of said analysis zone;
- first and second order statistical characteristics of the analysis zone;
- characteristics obtained by gradients of the analysis zone either in the whole of or in portions thereof;
- characteristics obtained by cascading;
- a characteristic orientation and a local phase of at least a portion of the analysis zone, wherein said extracting quantitative information comprises simultaneously extracting quantitative information corresponding to a plurality of characteristics, and further comprising selecting from a plurality of machine learning algorithms depending on the extracted characteristics and combining a plurality of algorithms to assess said condition of said tissue.

11. The method according to claim 10, wherein, for a specific condition to be assessed, the received image corresponds to a particular anatomical plane.

12. The method according to claim 10, further comprising selecting said characteristics calculated from a co-occurrence matrix from a list including first order statistics, an angular second moment, a contrast, a correlation, an energy and an entropy of said analysis zone.

13. The method according to claim 10, further comprising selecting said first and second order statistical characteristics of the analysis zone from a list including a mean value, a variance, a standard deviation, a skew and a kurtosis of the analysis zone.

14. A method of diagnosing a pathological condition of at least a portion of an animal or human tissue, comprising:
- receiving an image of said at least one portion of animal or human tissue;
- indicating an analysis zone in said received image;
- extracting quantitative information from said analysis zone;
- applying a machine learning algorithm to said extracted quantitative information to assess the condition of said tissue;

wherein said extracting quantitative information comprises compensating for a rotation of the analysis zone, wherein, if the extracted quantitative information corresponds to stored quantitative information belonging to animal or human tissue of said pathological condition, then said portion of animal or human tissue is diagnosed of said pathological condition, and wherein said extracting quantitative information comprises simultaneously extracting quantitative information corresponding to a plurality of characteristics.

15. The method according to claim 14, further comprising selecting from a plurality of machine learning algorithms depending on the extracted characteristics.

16. The method according to claim 15, further comprising combining a plurality of algorithms to assess said condition of said tissue.

17. The method according to claim 14, further comprising storing quantitative information corresponding to characteristics of a plurality of images corresponding to said condition.

* * * * *